(12) United States Patent
Lin et al.

(10) Patent No.: US 10,943,347 B2
(45) Date of Patent: Mar. 9, 2021

(54) IMAGE PROCESSING METHOD, APPARATUS, AND NON-TRANSITORY READABLE STORAGE MEDIUM

(71) Applicant: SHENZHEN IMSIGHT MEDICAL TECHNOLOGY CO. LTD, Shenzhen (CN)

(72) Inventors: Huangjing Lin, Shenzhen (CN); Qi Dou, Shenzhen (CN); Hao Chen, Shenzhen (CN)

(73) Assignee: SHENZHEN IMSIGHT MEDICAL TECHNOLOGY CO. LTD, Shenzhen (CN)

( * ) Notice: Subject to any disclaimer, the term of this patent is extended or adjusted under 35 U.S.C. 154(b) by 150 days.

(21) Appl. No.: 16/405,928

(22) Filed: May 7, 2019

(65) Prior Publication Data

US 2020/0005453 A1 Jan. 2, 2020

(30) Foreign Application Priority Data

Jun. 28, 2018 (CN) .......................... 201810695269.4

(51) Int. Cl.
*G06T 7/00* (2017.01)
*G06T 7/11* (2017.01)
*G06T 5/50* (2006.01)

(52) U.S. Cl.
CPC .............. *G06T 7/0012* (2013.01); *G06T 5/50* (2013.01); *G06T 7/11* (2017.01);
(Continued)

(58) Field of Classification Search
CPC ..................... G06T 7/0012; G06T 7/11; G06T 2207/20101; G06T 2207/20084;
(Continued)

(56) References Cited

U.S. PATENT DOCUMENTS

2017/0200067 A1\* 7/2017 Zhou ....................... G06T 7/174
2018/0129911 A1 5/2018 Madabhushi et al.
(Continued)

FOREIGN PATENT DOCUMENTS

| CN | 105574859 A | 5/2016 |
| CN | 107368670 A | 11/2017 |
| CN | 107545571 A | 1/2018 |

OTHER PUBLICATIONS

International Search Report in corresponding PCT Application PCT/CN2018/105235, dated Feb. 27, 2019.
(Continued)

*Primary Examiner* — Syed Haider
(74) *Attorney, Agent, or Firm* — Westbridge IP LLC

(57) ABSTRACT

Disclosed are an image processing method, an image processing apparatus, and a readable storage medium. First, an image to be processed is received, and the received image to be processed is divided into regions of interest by region segmentation means. Next, the regions of interest are detected by calling a pre-stored full convolution network structure model, to obtain probability image segments. Finally, the probability image segments are synthesized to generate a target probability image. Wherein, the pre-stored full convolution network structure model includes a full convolution structure. A linear regression layer is replaced by an equivalent convolution layer in the full convolution structure. A blank padding operation layer and an up-sampling layer are removed from the full convolution structure.

20 Claims, 7 Drawing Sheets

(52) U.S. Cl.
CPC ............... *G06T 2207/20084* (2013.01); *G06T 2207/20101* (2013.01); *G06T 2207/20221* (2013.01); *G06T 2207/30004* (2013.01)

(58) Field of Classification Search
CPC ........... G06T 2207/20221; G06T 2207/30004; G16H 30/40; G16H 50/20; G06K 9/6232; G06N 3/0454; G06N 3/082
See application file for complete search history.

(56) References Cited

U.S. PATENT DOCUMENTS

| | | | |
|---|---|---|---|
| 2018/0165551 A1* | 6/2018 | Roh | G06K 9/6267 |
| 2019/0114510 A1* | 4/2019 | Bremer | G06K 9/6271 |
| 2019/0171870 A1* | 6/2019 | Vajda | G06T 7/75 |
| 2019/0188525 A1* | 6/2019 | Choi | G06K 9/628 |
| 2019/0304095 A1* | 10/2019 | Veni | G06N 5/046 |

OTHER PUBLICATIONS

Lin, Huangjing et al., ScanNet: A Fast and Dense Scanning Framework for Metastatic Breast Cancer Detection from Whole-Slide Image, 2018 IEEE Winter Conference on Applications of Computer Vision, Mar. 15, 2018, pp. 539-546.

* cited by examiner

Table 1: The architecture of our proposed ScanNet.

| Layer | Features (Train) | Features (Predict) | Kernel size | Stride |
|---|---|---|---|---|
| Input | 244×244×3 | 2868×2868×3 | - | - |
| Conv1_1 | 242×242×64 | 2866×2866×64 | 3×3 | 1×1 |
| Conv1_2 | 240×240×64 | 2864×2864×64 | 3×3 | 1×1 |
| Pool1 | 120×120×64 | 1432×1432×64 | 2×2 | 2×2 |
| Conv2_1 | 118×118×128 | 1430×1430×128 | 3×3 | 1×1 |
| Conv2_2 | 116×116×128 | 1428×1428×128 | 3×3 | 1×1 |
| Pool2 | 58×58×128 | 714×714×128 | 2×2 | 2×2 |
| Conv3_1 | 56×56×256 | 712×712×256 | 3×3 | 1×1 |
| Conv3_2 | 54×54×256 | 710×710×256 | 3×3 | 1×1 |
| Conv3_3 | 52×52×256 | 708×708×256 | 3×3 | 1×1 |
| Pool3 | 26×26×256 | 354×354×256 | 2×2 | 2×2 |
| Conv4_1 | 24×24×512 | 352×352×512 | 3×3 | 1×1 |
| Conv4_2 | 22×22×512 | 350×350×512 | 3×3 | 1×1 |
| Conv4_3 | 20×20×512 | 348×348×512 | 3×3 | 1×1 |
| Pool4 | 10×10×512 | 174×174×512 | 2×2 | 2×2 |
| Conv5_1 | 8×8×512 | 172×172×512 | 3×3 | 1×1 |
| Conv5_2 | 6×6×512 | 170×170×512 | 3×3 | 1×1 |
| Conv5_3 | 4×4×512 | 168×168×512 | 3×3 | 1×1 |
| Pool5 | 2×2×512 | 84×84×512 | 2×2 | 2×2 |
| Conv6 | 1×1×1024 | 83×83×1024 | 2×2 | 1×1 |
| Conv7 | 1×1×1024 | 83×83×1024 | 1×1 | 1×1 |
| Conv8 | 1×1×2 | 83×83×2 | 1×1 | 1×1 |

FIG. 6

IMAGE PROCESSING METHOD, APPARATUS, AND NON-TRANSITORY READABLE STORAGE MEDIUM

FIELD

The present disclosure relates to the field of image technology, and more particularly relates to an image processing method, an image processing apparatus, and a readable storage medium.

BACKGROUND

In an existing technology of processing a pathological image, the pathological image is normally intercepted by a sliding window frame, to obtain image blocks. The image blocks are then input into a particular Convolutional Neural Network (CNN), to obtain prediction values thereof. The prediction values are finally stitched together to generate a probability image.

However, overlapping areas can hardly be avoided between adjacently intercepted image blocks. The prediction values are calculated with high redundancy. Thus, efficiency is low in processing the pathological image.

SUMMARY

The present disclosure relates to image processing. One aspect of the present disclosure relates to an image processing method. The method may be implemented on at least one machine each of which has at least one processor and one storage. The method may include one or more of the following operations. An image to be processed is received, the received image to be processed is divided into regions of interest by region segmentation means. The regions of interest are detected by calling a pre-stored full convolution network structure model, to obtain probability image segments. And the probability image segments are synthesized to generate a target probability image. Wherein, the pre-stored full convolution network structure model includes a full convolution structure. A linear regression layer is replaced by an equivalent convolution layer in the full convolution structure. A blank padding operation layer and an up-sampling layer are removed from the full convolution structure.

Another aspect of the present disclosure relates to an image processing apparatus. The image processing apparatus includes a memory, a processor, a communication bus, and an image processing program stored in the memory. The communication bus is configured to implement communication connection between the processor and the memory. The processor is configured to execute the image processing program, in order to perform the operations of the image processing method.

Another aspect of the present disclosure relates to a readable storage medium. The readable storage medium stores an image processing program. The image processing program, when executed by a processor, may cause the processor to perform the operations of the image processing method.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

FIG. 6 is a third scene illustration of the image processing method according to the present disclosure, which illustrates an exemplary process for processing the region of interest by the transformed full convolution network structure model;

DETAILED DESCRIPTION OF THE EMBODIMENTS

In the following detailed description, numerous specific details are set forth by way of embodiments in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

Figure 1:
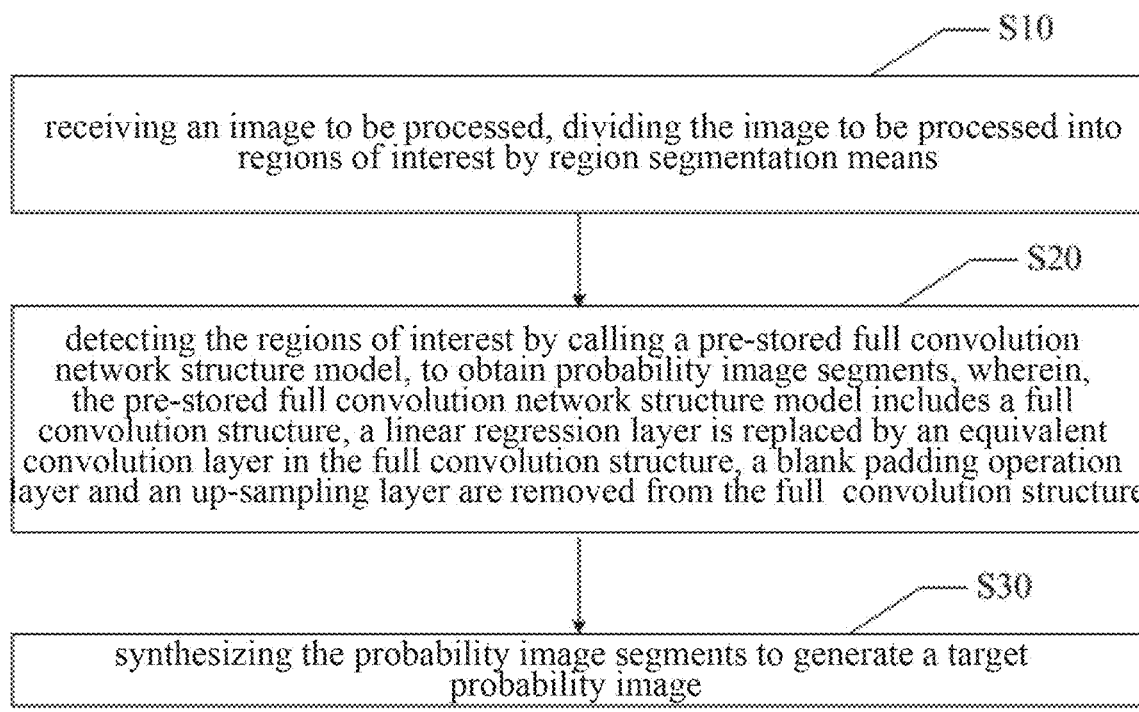
FIG. 1 is a flowchart illustrating a first embodiment of an image processing method according to the present disclosure.

Referring to FIG. 1, an image processing method according to a first embodiment of the present disclosure may include steps S10 to S30 as follows.

In S10, receiving an image to be processed, and dividing the image to be processed into regions of interest by region segmentation means.

It should be noted that, the image processing method according to the present disclosure is applied to the pathological image processing. In some embodiments, the step S10 may include steps S11 to S12.

In S11, receiving the image to be processed, and obtaining a tissue region by retrieving the image to be processed based on an adaptive threshold maximum inter-class variance algorithm.

In S12, obtaining a current video memory capacity, and dividing the tissue region into the regions of interest by using a divide-and-conquer algorithm, according to the current video memory capacity.

Figure 4:
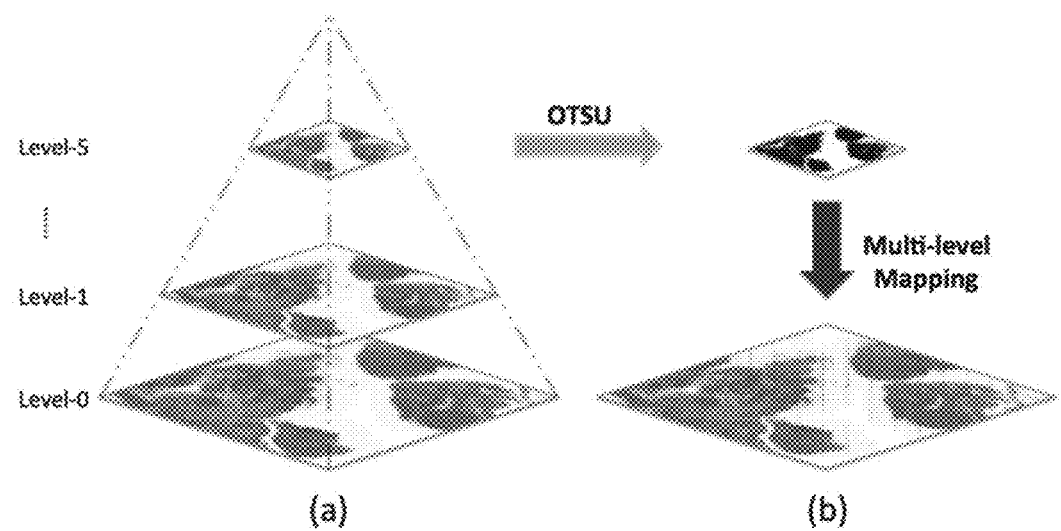
FIG. 4 is a first scene illustration of the image processing method according to the present disclosure, which illustrates an exemplary process for obtaining the tissue region.

In this embodiment, the regions of interest are obtained by using the "divide-and-conquer" algorithm in the process of image region segmentation, as shown in FIG. 4. The image to be processed is received, and the tissue region is obtained by retrieving the image to be processed in a low resolution zone-5 (Level-5), based on the adaptive threshold maximum inter-class variance algorithm (OTSU). The adaptive threshold maximum inter-class variance algorithm is used to, according to grayscale characteristics, divide the image to be processed into foreground image and background image to extract characteristic information, so as to obtain the tissue region. The obtained tissue region is positioned to a high resolution zone-0 (Level-0). And the whole of the tissue region is divided into the regions of interest of particular shapes by using the divide-and-conquer algorithm.

In this embodiment, the video memory capacity corresponding to a current image processing apparatus is obtained in advance. The tissue region is divided into the regions of interest by using the divide-and-conquer algorithm, according to the obtained video memory capacity. As such, the regions of interest are zoomed in or zoomed out to corresponding sizes according to the video memory capacity in actual image processing. Thus, the redundancy of calculation is reduced, and the efficiency in processing the pathological image is improved.

In S20, detecting the regions of interest by calling a pre-stored full convolution network structure model to obtain probability image segments; wherein, the pre-stored full convolution network structure model includes a full convolution structure, a linear regression layer is replaced by an equivalent convolution layer in the full convolution structure, a blank padding operation layer and an up-sampling layer are removed from the full convolution structure.

In some embodiments, the step S20 may be implemented as follows:
detecting each of the regions of interest in parallel by calling the pre-stored full convolution network structure model, to obtain each of the probability image segments.

In some embodiments, the regions of interest are detected by the pre-stored full convolution network structure model in parallel, rather than by an existing model such as VGG-16. The model VGG-16 is a deep convolution neural network model developed by the Visual Geometry Group at the University of Oxford. The pre-stored full convolution network structure model is new compared to the model VGG-16. Specifically, the full convolution structure corresponding to the pre-stored full convolution network structure model does not include the blank padding operation layer or any of the up-sampling layers. Thus, the pre-stored full convolution network structure model does not perform the blank padding operation or the up-sampling operation on the regions of interest. In addition, the linear regression layer is replaced by the equivalent convolution layer in the full convolution structure corresponding to the pre-stored full convolution network structure model.

Taking a specific example for illustration, the linear regression layer in the convolution model such as VGG-16 is replaced with a convolution layer of 1×1×n shape, to perform the full convolution operation on the regions of interest. As shown in FIG. 6, "Layer" refers to a convolution layer; "Input" refers to an input image, which may be the regions of interest; "Kernel size" refers to the size of a convolution kernel; "Stride" refers to a stride; each "Conv" represents one convolution layer, for example, the first layer has two layers of convolution layers as Conv1_1 and Conv1_2, the third layer has three layers of convolution layers as Conv3_1, Conv3_2 and Conv3_3; and "Pool" refers to pooling, such as "Pool1" and "Pool2" refer to the first pooling and the second pooling respectively. In this drawing, first, the convolution operation is performed twice on the regions of interest by using a 3*3 convolution kernel; then, the activation pooling operation is performed; and after multiple times of convolution and activation pooling, the probability image segments are obtained.

According to the present disclosure, the full convolution operation is performed on each of the regions of interest, while no blank padding operation is performed. In this way, large-size image processing can be realized, and redundant interceptions made on the image to be processed are decreased. Thus, the redundancy of calculation is reduced, and the efficiency in processing the pathological image is improved.

In the prior art, improving the efficiency in processing the pathological image may result in a decrease of the scanning accuracy or the scanning density, furthermore weakening the sensitivity of the pr-stored full convolution network structure model. In order to avoid this, in some embodiments, the densification detection is performed on the image to be processed by the pre-stored full convolution network structure model after the model transformation. It should be noted that, the densification times or the densification degree depends on detection requirements of the image to be processed.

Figure 2:
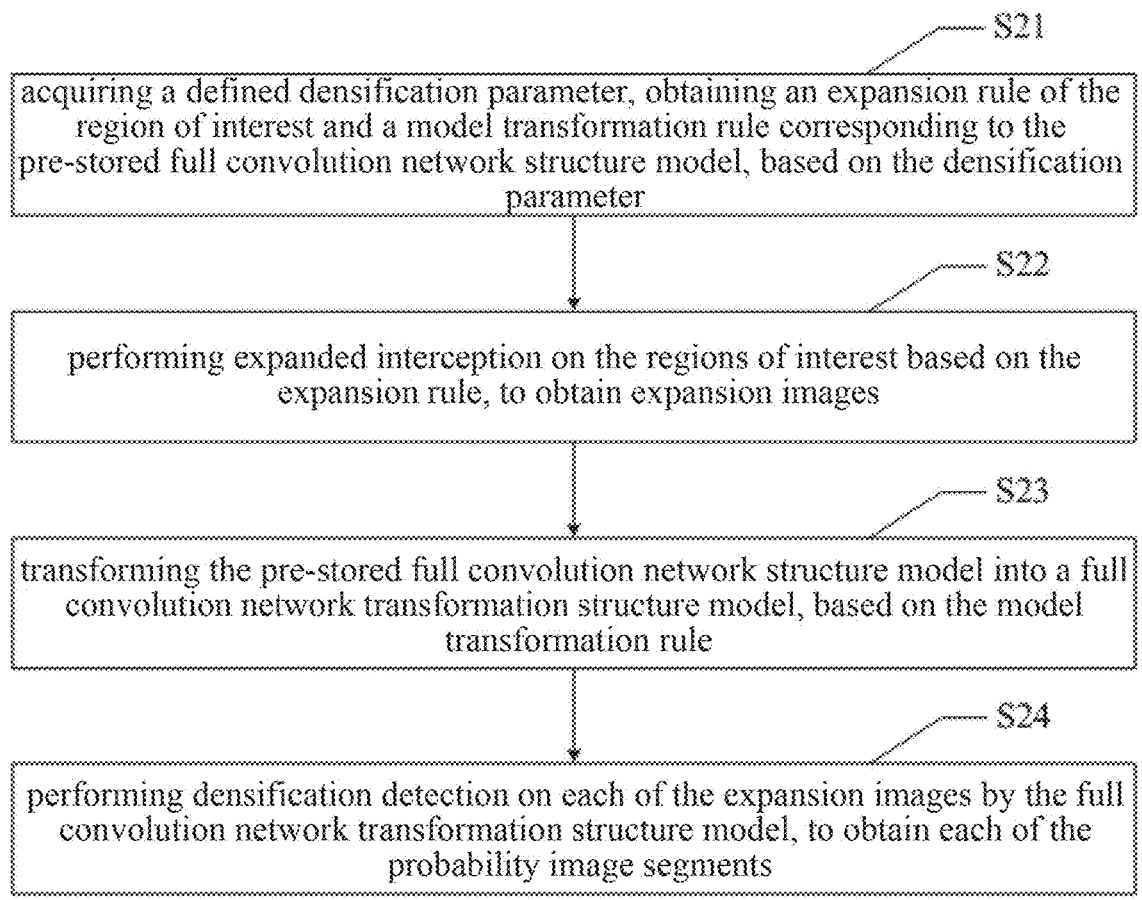
FIG. 2 is a flowchart illustrating an exemplary process for detecting the regions of interest by calling a pre-stored full convolution network structure model to obtain probability image segments in the image processing method according to the present disclosure.

As shown in FIG. 2, the step S20 may include steps S21 to S24 as follows.

In S21, acquiring a defined densification parameter, and obtaining an expansion rule of the region of interest and a model transformation rule corresponding to the pre-stored full convolution network structure model, based on the densification parameter.

The densification parameter may vary with the image to be processed. In some embodiments, the densification parameter is determined and input by a user according to the detection requirements after viewing the image to be processed. The expansion rule, and the model transformation rule corresponding to the pre-stored full convolution network structure model may be obtained according to the densification parameter.

Specifically, the model transformation rule may include a backtracking convolution rule, and the step S21 may include steps S211 to S212 as follows.

In S211, obtaining a densification times and an equivalent scan stride based on the densification parameter, to calculate the expansion rule of the region of interest.

In S212, obtaining an anchor point stride, a convolution kernel moving distance, and a convolution dilation rate required for transformation of each layer in the pre-stored full convolution network structure model based on the densification parameter, to obtain the backtracking convolution rule.

In S22, performing expanded interception on the regions of interest based on the expansion rule, to obtain expansion images.

In S23, transforming the pre-stored full convolution network structure model into a full convolution network transformation structure model, based on the model transformation rule.

In S24, performing densification detection on each of the expansion images by the full convolution network transformation structure model, to obtain each of the probability image segments.

In this embodiment, the backtracking full convolution network structure model is obtained by the model transformation using the backtracking convolution rule. It should be understood that, the model transformation rule in the present disclosure is not limited to the backtracking convolution rule. The backtracking full convolution network structure model includes an anchor point backtracking layer (Anchor Layer or AnchLayer). The AnchLayer includes an anchor point backtracking convolution layer (AnchConv) and an anchor point backtracking de-sampling layer (AnchPool). Different from the existing convolution layer and the de-sampling layer, the anchor point backtracking layer includes an operation of setting parameters. The parameters to be set correspond to the transformation of each layer, such as the anchor point stride $S_a$, the convolution kernel moving distance $d_a$, and the convolution dilation rate.

Figure 7:
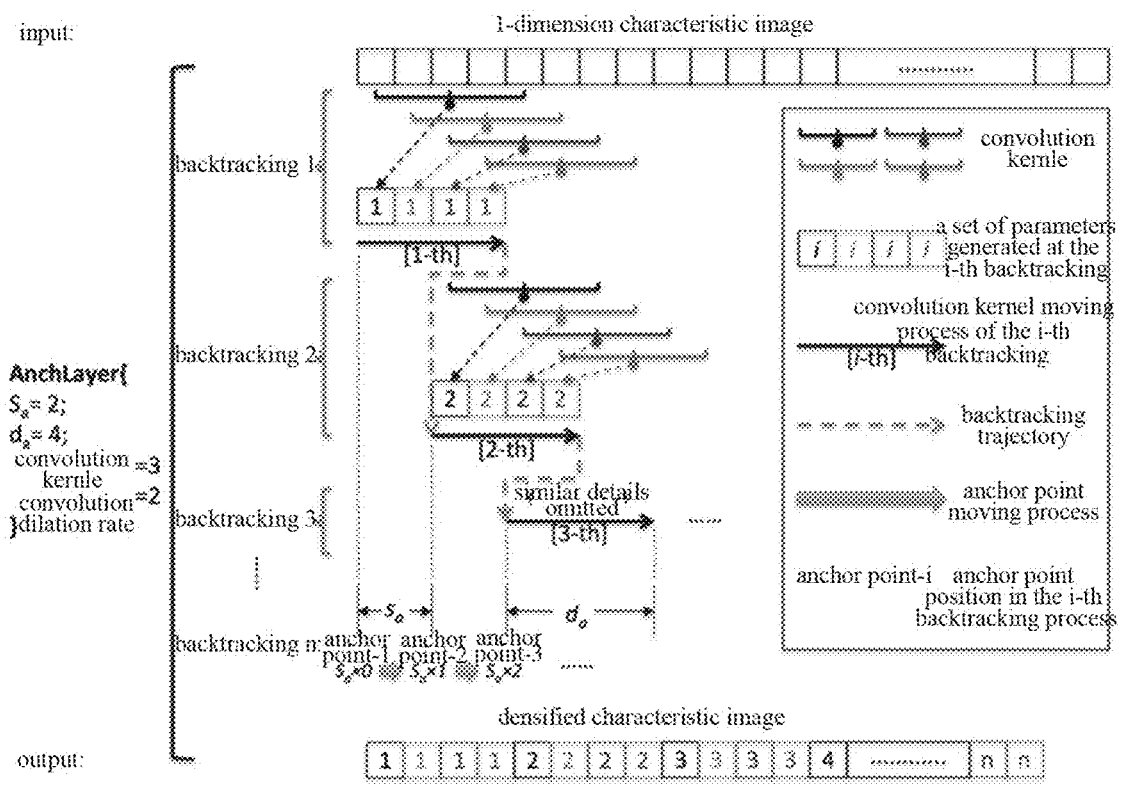
FIG. 7 is a fourth scene illustration of the image processing method according to the present disclosure, which illustrates the backtracking convolution with the anchor point.

As shown in FIG. 7, in each backtracking iteration, the convolution kernel completes the convolution operation corresponding to the current iteration with distance $d_a$, after that the convolution kernel backtracks to a corresponding anchor point position for the next iteration. It should be noted that, the anchor point proceeds forward stride $S_a$, each time, and the convolution dilation rate is calculated by interval sampling of the convolution kernel in the backtracking iteration, so as to finally implement the detection of the regions of interest.

Specifically, the regions of interest are expandedly intercepted by using the expansion rule, before the backtracking full convolution network structure model performs the densification detection on the regions of interest. The expansion rule of each region of interest is calculated with the densification times and the equivalent scan stride which are obtained based on the densification parameter. The expansion rule mainly includes an expansion length required for the expanded interception. The expansion length of the expanded interception is relative to an interception length used in the traditional model such as VGG-16. In some embodiments, the expanded length of the expanded interception used on each region of interest is expressed as $L_e=(\alpha-1)\times S_f/\alpha$, wherein, $\alpha$ is the densification times, $S_f$ is the correspondingly equivalent scan stride, namely the equivalent scan stride, when the pre-stored full convolution network structure model is compared to the traditional sliding window model such as VGG-16. That is, the scan stride of the pre-stored full convolution network structure model is $1/\alpha$ times smaller than the scan stride of the traditional sliding window model. For example, if the equivalent scan stride corresponding to the traditional sliding window model is $S_f=32$, the scan stride for the densification is $S'_f=16$, namely $\alpha=2$, then the expansion length is defined as $L_e=(\alpha-1)\times S_f/\alpha=24$. It should be noted that, the specific expansion rule is determined before the model transformation. In some embodiments, the expansion rule is obtained after the regions of interest are received. Thus, the regions of interest are expandedly intercepted based on the obtained expansion rule, to obtain the expansion images.

The defined densification parameter corresponding to each expansion image is obtained, after each expansion image is obtained. The model transformation rule corresponding to the pre-stored full convolution network structure model is obtained, based on the densification parameter. In some embodiments, the model transformation rule is the backtracking convolution rule. Specifically, the backtracking convolution rule may be obtained by acquiring the anchor point stride, the convolution kernel moving distance, and the convolution dilation rate. In this embodiment, the parameters corresponding to the backtracking convolution rule should satisfy conditions as follows:

$$\begin{cases} S_a = S_s \times \alpha \\ d_a = \alpha \end{cases}$$

Figure 8:
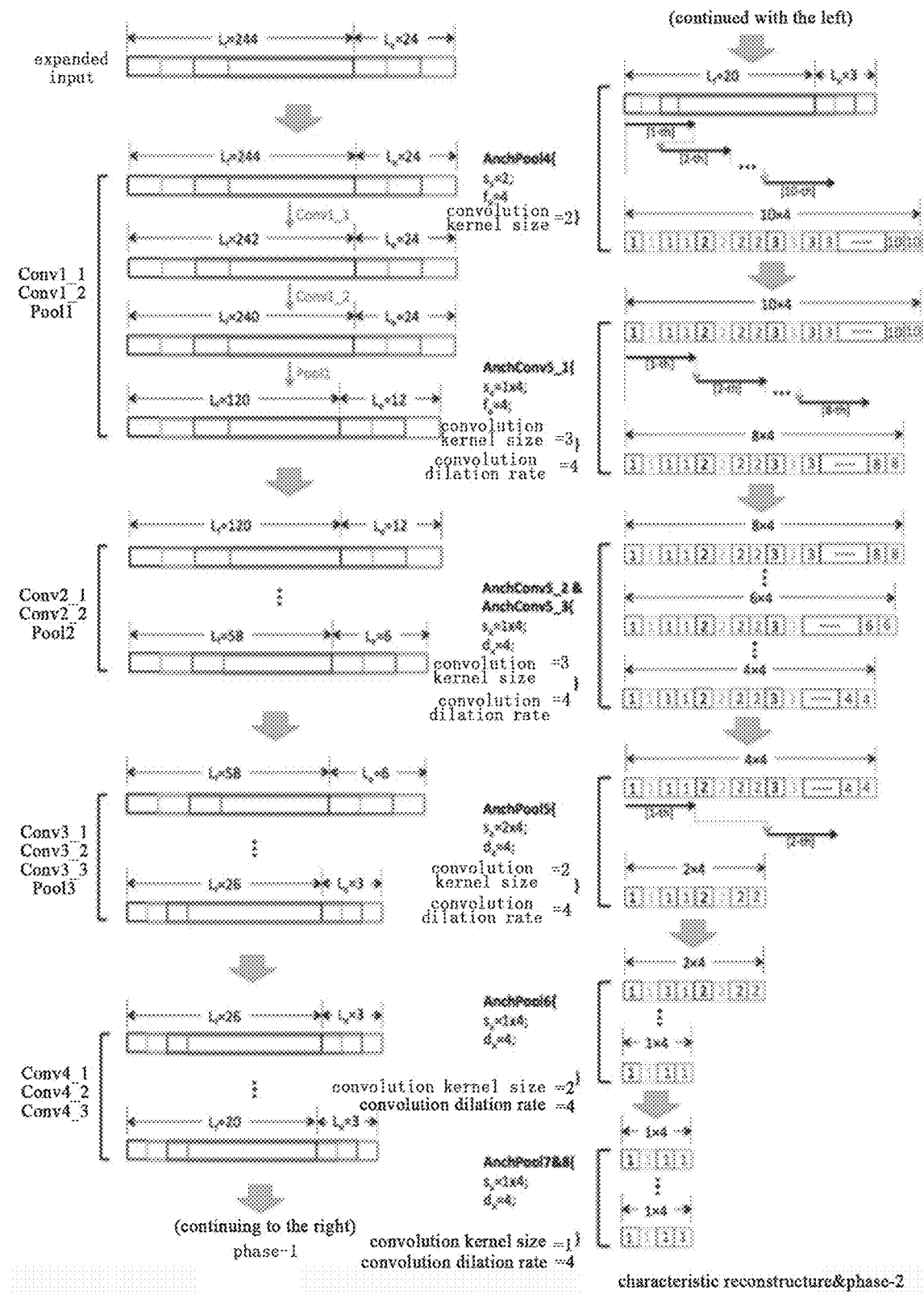
FIG. 8 is a fifth scene illustration of the image processing method according to the present disclosure, which illustrates the densification detection on the region of interest by the transformed full convolution network structure model.

Wherein, $\alpha$ is the densification coefficient, $S_a$ is the anchor point stride corresponding to the backtracking full convolution network structure model after the model transformation, $S_s$ is the convolution kernel stride corresponding to the pre-stored full convolution network model before the model transformation, $d_a$ is the convolution kernel moving distance corresponding to the backtracking full convolution network structure model after the model transformation. The backtracking full convolution network structure model is obtained by the model transformation using the backtracking convolution rule. Each of the expansion images is detected by the backtracking fill convolution network structure model, to obtain each of the probability image segments. $\alpha^N$ times the densification probability image (N is the number of dimensions) are obtained, after the densification detection on each of the expansion images by the backtracking full convolution network structure model. Referring to the specific process as shown in FIG. 8, each Cony represents one convolution layer.

It should be noted that, the original convolution layer may also be preserved before the model transformation. If the convolution operation and the down-sampling calculation on the expansion image can be performed normally by the full convolution network structure model, then no structural change is needed to the original convolution layer and the down-sampling layer corresponding to the full convolution network structure model. That is, their structures are preserved. If the convolution operation and the down-sampling calculation on the expansion image can not be performed normally, for example, it is unable to continue performing the convolution and the down-sampling operation on the expansion image, then the model transformation is performed. That is, the convolution layer transformation is performed.

In this embodiment, the densification detection is performed after the model transformation. By this way, the efficiency in processing the pathological image is improved, and also the scanning accuracy or the scanning density is ensured. Thus, the sensitivity reduction of the model is avoided.

In S30, synthesizing the probability image segments to generate a target probability image.

In some embodiments, the target probability image is taken as a global probability image.

In addition, after the step S30, the image processing method further includes:

removing a singular point from the target probability image using a morphological opening operation rule; and outputting the target probability image after removing the singular point.

Figure 5:
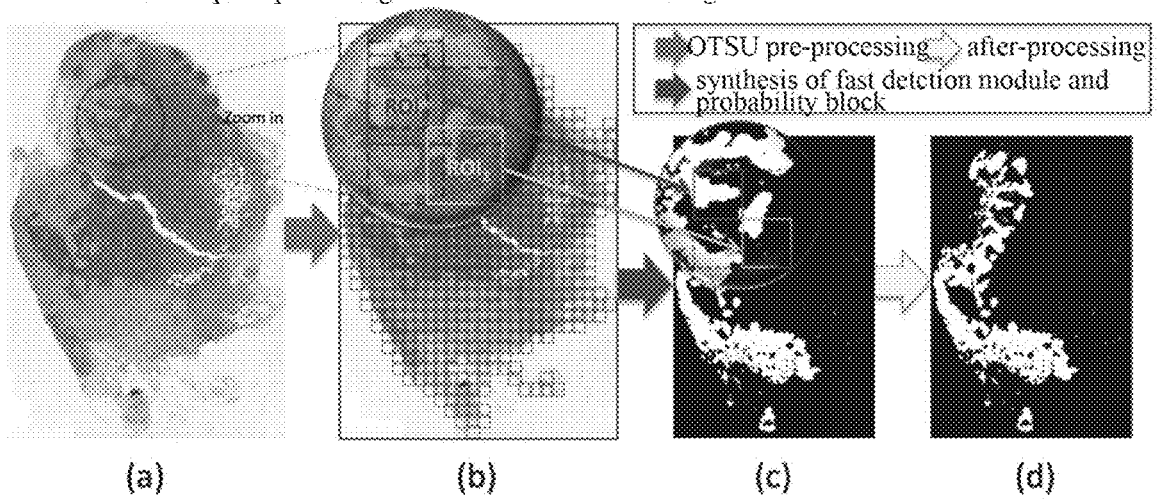
FIG. 5 is a second scene illustration of the image processing method according to the present disclosure, which illustrates an exemplary process for processing the tissue region to obtain the probability image by using the divide-and-conquer algorithm.

As shown in FIG. 5, the singular point in the target probability image is obtained by using the morphological opening operation rule. The target probability image after removing the singular point is output. It should be noted that, the removal of the singular point is known in the prior art, thus it is not to be detailed herein.

In the present disclosure, the image to be processed is divided into the regions of interest by performing the image region segmentation. The regions of interest are detected by the pre-stored full convolution network structure model, to obtain the probability image segments. And the target probability image is generated by synthesizing the probability image segments. Different from the traditional convolution network structure model, the pre-stored full convolution network structure model includes the full convolution structure. Wherein, the linear regression layer is replaced by the equivalent convolution layer in the full convolution structure, the blank padding operation layer and the up-sampling layer are removed from the full convolution structure. Thus, no blank padding is performed on the regions of interest in the full convolution operation. As such, large-size image processing can be realized. Due to this, redundant interceptions made on the image to be processed are decreased. According to the present disclosure, the redundancy of calculation is reduced, and the efficiency in processing the pathological image is improved.

Further, the present disclosure provides another embodiment of the image processing method. In some embodiments, the step S20 may include steps S25 to S27 as follows.

In S25, obtaining a defined offset densification coefficient and offset densification dimension information, to calculate an offset times and a unit length of a single offset corresponding to each of the regions of interest.

In S26, offsetting each of the regions of interest based on the offset times and the unit length of the single offset, to obtain each of offset regions of interest.

In S27, detecting the offset regions of interest by calling the pre-stored full convolution network structure model, to obtain the offset probability image segments.

In some embodiments, the step S30 may include steps S31 to S32 as follows.

In S31, stitching the probability image segments interleavingly, to reconstruct a densification probability image.

In S32, taking the densification probability image as the target probability image.

Figure 9:
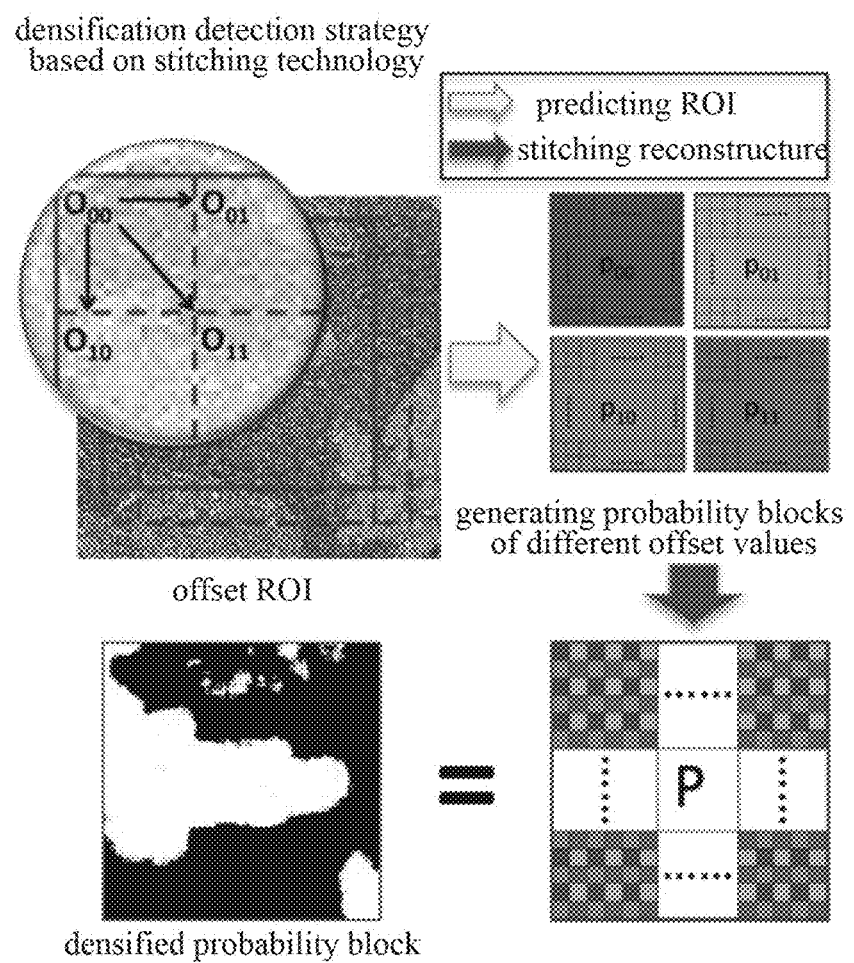
FIG. 9 is a sixth scene illustration of the image processing method according to the present disclosure, which illustrates the densification detection on the regions of interest by the transformed full convolution network structure model based on the stitching technology.

In this embodiment, another densification image processing strategy is provided as shown in FIG. 9. The defined offset densification coefficient and the offset densification dimension information are obtained, to calculate the offset times and the unit length of the single offset corresponding to each region of interest. Each region of interest is offset based on the offset times and the unit length of the single offset, to obtain each of offset regions of interest. It should be noted that, the unit length of the single offset is relative to the pre-stored full convolution network structure model before the model transformation. For example, if the sliding stride corresponding to the pre-stored full convolution network structure model before the model transformation is expressed as $S_f=32$, the dimension is expressed as N=2, and the densification coefficient is expressed as $\alpha=2$, then the offset times is $(\alpha-1)=1$, the unit length of the single offset is $S_f/\alpha=32/2=16$, and a total of $\alpha^N=2^2=4$ offset regions of interest with different offset values are obtained. The dimension, the densification coefficient and the sliding stride are predetermined or obtained.

It should be noted that, the specific offset times and the unit length of the single offset are pre-determined, when processing the regions of interest. As such, each of the regions of interest can be directly offset according to the offset times and the unit length of the single offset. Each of the offset regions of interest is input into the pre-stored full convolution network structure model for detection, so as to obtain each of the offset probability image segments. The specific process of detecting each of the regions of interest is basically the same as the first embodiment above, which is not to be detailed herein again.

It should be noted that, after obtaining each of the offset probability image segments, the step S30 may include steps:

stitching the probability image segments interleavingly, to reconstruct a densification probability image; and taking the densification probability image as the target probability image.

The densification process is shown in FIG. 9, wherein the dimension N=2, the densification coefficient $\alpha=2$. The interleaving stitching is performed on the $\alpha^N$ second class probability images, to reconstruct the densified probability image. The interleaving stitching does not increase the video memory capacity of the image processing apparatus. Therefore, the efficiency of processing the pathological image is improved. Also, the scanning accuracy or the scanning density is ensured, and the sensitivity reduction of the model is avoided.

It should be noted that, in the present disclosure, the regions of interest are offset, and the offset regions of interest are then input into the full convolution network transformation structure model. The full convolution network transformation structure model performs the densification detection on the offset regions of interest.

The present disclosure also provides an image processing apparatus. In some embodiments, the image processing apparatus may be a personal computer (PC), a portable computer, or a terminal device such as a mobile device.

Figure 3:
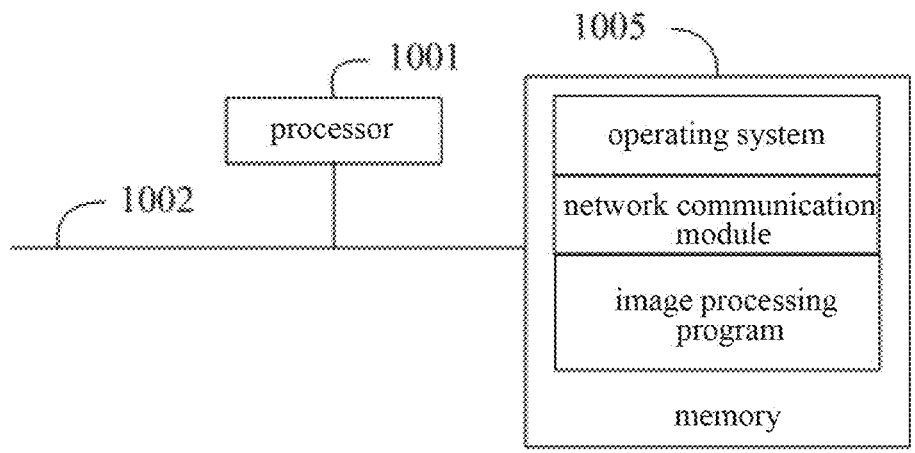
FIG. 3 is an apparatus structure diagram of hardware operating environment involved in the embodiments according to the present disclosure.

As shown in FIG. 3, the image processing apparatus may include a processor 1001 such as a CPU, a memory 1005, and a communication bus 1002. The communication bus 1002 is configured to facilitate connection and communication between the processor 1001 and the memory 1005. The memory 1005 may be a high-speed RAM memory, or a non-volatile memory such as a disk memory. The memory 1005 optionally may also be a storage device that is separate from the processor 1001 described above.

In some embodiments, the image processing apparatus may further include a user interface, a network interface, a camera, an RF (Radio Frequency) circuitry, a sensor, an audio circuitry, a WiFi module, and the like. The user interface may include a display, an input unit such as a keyboard, and an optional user interface may also include a standard wired interface and wireless interface. The network interface may optionally include a standard wired interface and wireless interface (such as a WI-FI interface).

Those skilled in the art can understand that the structure of the image processing apparatus illustrated in FIG. 3 does not constitute a limitation on the image processing apparatus. Thus, the image processing apparatus may include more or less components than those illustrated, or some components may be combined, or different arrangements of components may be employed.

As shown in FIG. 3, the memory 1005 as a computer storage medium may include an operating system, a network communication module, and an image processing program. The operating system is a program that manages and controls hardware and software resources of the image processing apparatus, and supports the operation of the image processing program and other software and/or programs. The network communication module is configured to facilitate the communication between various components within the memory 1005, and with other hardware and software in the image processing apparatus.

In the image processing apparatus shown in FIG. 3, the processor 1001 is configured to execute the image processing program stored in the memory 1005, so as to perform the steps of any of the above image processing methods.

The embodiments of the image processing apparatus according to the present disclosure are basically the same as the embodiments of the above image processing method. Thus, they are not to be detailed herein again.

The present disclosure also provides an image processing device. The image processing device includes a receiving module, a detecting module, and a synthesis module. The receiving module is configured to receive an image to be processed, and divide the image to be processed into regions of interest by region segmentation means. The detecting module is configured to detect the regions of interest by calling a pre-stored full convolution network structure model, to obtain probability image segments. And the synthesis module is configured to synthesize the probability image segments to generate a target probability image. Wherein, the pre-stored full convolution network structure model includes a full convolution structure. A linear regression layer is replaced by an equivalent convolution layer in the full convolution structure. A blank padding operation layer and an up-sampling layer are removed from the full convolution structure.

The embodiments of the image processing device according to the present disclosure are basically the same as the embodiments of the above image processing method. Thus, they are not to be detailed herein again.

The present disclosure also provides a readable storage medium. The readable storage medium stores an image processing program, which can be executed by a processor to perform the steps of any of the above image processing methods.

The embodiments of the readable storage medium according to the present disclosure are basically the same as the embodiments of the above image processing method, thus they are not to be detailed herein again.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. An image processing method, comprising:
    receiving an image to be processed, dividing the image to be processed into regions of interest by region segmentation means;
    detecting the regions of interest by calling a pre-stored full convolution network structure model, to obtain probability image segments, wherein, the pre-stored full convolution network structure model comprises a full convolution structure, a linear regression layer is replaced by an equivalent convolution layer in the full convolution structure, a blank padding operation layer and an up-sampling layer are removed from the full convolution structure; and
    synthesizing the probability image segments to generate a target probability image.

2. The method of claim 1, wherein the operation of detecting the regions of interest by calling a pre-stored full convolution network structure model, to obtain probability image segments comprises:
    acquiring a defined densification parameter, obtaining an expansion rule of the region of interest and a model transformation rule corresponding to the pre-stored full convolution network structure model, based on the densification parameter;
    performing expanded interception on the regions of interest based on the expansion rule, to obtain expansion images;
    transforming the pre-stored full convolution network structure model into a full convolution network transformation structure model, based on the model transformation rule; and
    performing densification detection on each of the expansion images by the full convolution network transformation structure model, to obtain each of the probability image segments.

3. The method of claim 2, wherein the model transformation rule comprises a backtracking convolution rule;
    the operation of obtaining an expansion rule of the region of interest and a model transformation rule corresponding to the pre-stored full convolution network structure model, based on the densification parameter comprises:
    obtaining a densification times and an equivalent scan stride based on the densification parameter, to calculate the expansion rule of the region of interest; and
    obtaining an anchor point stride, a convolution kernel moving distance, and a convolution dilation rate required for transformation of each layer in the pre-stored full convolution network structure model based on the densification parameter, to obtain the backtracking convolution rule.

4. The method of claim 1, wherein the operation of detecting the regions of interest by calling a pre-stored full convolution network structure model, to obtain probability image segments comprises:
    obtaining a defined offset densification coefficient and offset densification dimension information, to calculate an offset times and a unit length of a single offset corresponding to each of the regions of interest;
    offsetting each of the regions of interest based on the offset times and the unit length of the single offset, to obtain each of offset regions of interest;
    detecting the offset regions of interest by calling the pre-stored full convolution network structure model, to obtain the offset probability image segments;
    the operation of synthesizing the probability image segments to generate a target probability image comprises:
    stitching the probability image segments interleavingly, to reconstruct a densification probability image; and
    taking the densification probability image as the target probability image.

5. The method of claim 1, wherein the operation of receiving an image to be processed, dividing the image to be processed into regions of interest by region segmentation means comprises:

receiving the image to be processed, obtaining a tissue region by retrieving the image to be processed, based on an adaptive threshold maximum inter-class variance algorithm; and obtaining a current video memory capacity, dividing the tissue region into the regions of interest by using a divide-and-conquer algorithm, according to the current video memory capacity.

6. The method of claim 1, wherein after the operation of synthesizing the probability image segments to generate a target probability image, the method further comprises:

removing a singular point from the target probability image using a morphological opening operation rule; and outputting the target probability image after removing the singular point.

7. The method of claim 1, wherein the operation of detecting the regions of interest by calling a pre-stored full convolution network structure model, to obtain probability image segments comprises:

detecting each of the regions of interest in parallel by calling the pre-stored full convolution network structure model, to obtain each of the probability image segments.

8. An image processing apparatus, wherein, the image processing apparatus comprises a memory, a processor, a communication bus, and an image processing program stored in the memory, the communication bus is configured to implement communication connection between the processor and the memory;

the processor is configured to execute the image processing program, in order to perform the following operations:

receiving an image to be processed, dividing the image to be processed into regions of interest by region segmentation means;

detecting the regions of interest by calling a pre-stored full convolution network structure model, to obtain probability image segments, wherein, the pre-stored full convolution network structure model comprises a full convolution structure, a linear regression layer is replaced by an equivalent convolution layer in the full convolution structure, a blank padding operation layer and an up-sampling layer are removed from the full convolution structure; and synthesizing the probability image segments to generate a target probability image.

9. The apparatus of claim 8, wherein the operation of detecting the regions of interest by calling a pre-stored full convolution network structure model, to obtain probability image segments comprises:

acquiring a defined densification parameter, obtaining an expansion rule of the region of interest and a model transformation rule corresponding to the pre-stored full convolution network structure model, based on the densification parameter;

performing expanded interception on the regions of interest based on the expansion rule, to obtain expansion images;

transforming the pre-stored full convolution network structure model into a full convolution network transformation structure model, based on the model transformation rule; and performing densification detection on each of the expansion images by the full convolution network transformation structure model, to obtain each of the probability image segments.

10. The apparatus of claim 9, wherein the model transformation rule comprises a backtracking convolution rule;

the operation of obtaining an expansion rule of the region of interest and a model transformation rule corresponding to the pre-stored full convolution network structure model, based on the densification parameter comprises:

obtaining a densification times and an equivalent scan stride based on the densification parameter, to calculate the expansion rule of the region of interest; and obtaining an anchor point stride, a convolution kernel moving distance, and a convolution dilation rate required for transformation of each layer in the pre-stored full convolution network structure model based on the densification parameter, to obtain the backtracking convolution rule.

11. The apparatus of claim 8, wherein the operation of detecting the regions of interest by calling a pre-stored full convolution network structure model, to obtain probability image segments, comprises:

obtaining a defined offset densification coefficient and offset densification dimension information, to calculate an offset times and a unit length of a single offset corresponding to each of the regions of interest;

offsetting each of the regions of interest based on the offset times and the unit length of the single offset, to obtain each of offset regions of interest;

detecting the offset regions of interest by calling the pre-stored full convolution network structure model, to obtain the offset probability image segments;

the operation of synthesizing the probability image segments to generate a target probability image comprises:

stitching the probability image segments interleavingly, to reconstruct a densification probability image; and taking the densification probability image as the target probability image.

12. The apparatus of claim 8, wherein the operation of receiving an image to be processed, and region dividing the image to be processed, to obtain regions of interest comprises:

receiving the image to be processed, obtaining a tissue region by retrieving the image to be processed, based on an adaptive threshold maximum inter-class variance algorithm; and obtaining a current video memory capacity, dividing the tissue region into the regions of interest by using a divide-and-conquer algorithm, according to the current video memory capacity.

13. The apparatus of claim 8, wherein after the operation of synthesizing the probability image segments to generate a target probability image, the processor is further configured to execute the image processing program to perform the following operations:

removing a singular point from the target probability image using a morphological opening operation rule; and outputting the target probability image after removing the singular point.

14. The apparatus of claim 8, wherein the operation of detecting the regions of interest by calling a pre-stored full convolution network structure model to obtain probability image segments comprises:

detecting each of the regions of interest in parallel by calling the pre-stored full convolution network structure model, to obtain each of the probability image segments.

15. A non-transitory readable storage medium, wherein, the non-transitory readable storage medium stores an image processing program, the image processing program when being executed by a processor performs the following operations:

receiving an image to be processed, dividing the image to be processed into regions of interest by region segmentation means;

detecting the regions of interest by calling a pre-stored full convolution network structure model, to obtain probability image segments, wherein, the pre-stored full convolution network structure model comprises a full convolution structure, a linear regression layer is replaced by an equivalent convolution layer in the full convolution structure, a blank padding operation layer and an up-sampling layer are removed from the full convolution structure; and synthesizing the probability image segments to generate a target probability image.

16. The non-transitory readable storage medium of claim 15, wherein the operation of detecting the regions of interest by calling a pre-stored full convolution network structure model, to obtain probability image segments comprises:

acquiring a defined densification parameter, obtaining an expansion rule of the region of interest and a model transformation rule corresponding to the pre-stored full convolution network structure model, based on the densification parameter;

performing expanded interception on the regions of interest based on the expansion rule, to obtain expansion images;

transforming the pre-stored full convolution network structure model into a full convolution network transformation structure model, based on the model transformation rule; and performing densification detection on each of the expansion images by the full convolution network transformation structure model, to obtain each of the probability image segments.

17. The non-transitory readable storage medium of claim 16, wherein the model transformation rule comprises a backtracking convolution rule, the operation of obtaining an expansion rule of the region of interest and a model transformation rule corresponding to the pre-stored full convolution network structure model, based on the densification parameter comprises:

obtaining a densification times and an equivalent scan stride based on the densification parameter, to calculate the expansion rule of the region of interest; and obtaining an anchor point stride, a convolution kernel moving distance, and a convolution dilation rate required for transformation of each layer in the pre-stored full convolution network structure model based on the densification parameter, to obtain the backtracking convolution rule.

18. The non-transitory readable storage medium of claim 17, wherein the operation of detecting the regions of interest by calling a pre-stored full convolution network structure model, to obtain probability image segments comprises:

obtaining a defined offset densification coefficient and offset densification dimension information, to calculate an offset times and a unit length of a single offset corresponding to each of the regions of interest;

offsetting each of the regions of interest based on the offset times and the unit length of the single offset, to obtain each of offset regions of interest;

detecting the offset regions of interest by calling the pre-stored full convolution network structure model, to obtain the offset probability image segments;

the operation of synthesizing the probability image segments to generate a target probability image comprises:

stitching the probability image segments interleavingly, to reconstruct a densification probability image; and taking the densification probability image as the target probability image.

19. The non-transitory readable storage medium of claim 16, wherein the operation of receiving an image to be processed, and dividing the image to be processed into regions of interest by region segmentation means comprises:

receiving the image to be processed, obtaining a tissue region by retrieving the image to be processed, based on an adaptive threshold maximum inter-class variance algorithm; and obtaining a current video memory capacity, dividing the tissue region into the regions of interest by using a divide-and-conquer algorithm, according to the current video memory capacity.

20. The non-transitory readable storage medium of claim 16, wherein after the operation of synthesizing the probability image segments to generate a target probability image, the image processing program when being executed by the processor further performs the following operations:

removing a singular point from the target probability image using a morphological opening operation rule; and outputting the target probability image after removing the singular point.

* * * * *